US011278581B2

(12) United States Patent
Parks et al.

(10) Patent No.: US 11,278,581 B2
(45) Date of Patent: Mar. 22, 2022

(54) USE OF VAGINAL *LACTOBACILLI* FOR IMPROVING THE SUCCESS RATE OF IN VITRO FERTILIZATION

(71) Applicants: Osel, Inc., Mountain View, CA (US); Aarhus Universitet, Aarhus C (DK); Region Midtjylland, Viborg (DK); Statens Serum Institut, Copenhagen S (DK)

(72) Inventors: Thomas P. Parks, San Mateo, CA (US); Peter Humaidan, Viborg (DK); Jørgen Skov Jensen, Søborg (DE); Niels Uldbjerg, Aarhus V (DK); Thor Haahr, Aarhus N (DK)

(73) Assignee: Osel, Inc., Mountain View, CA (US)

(*) Notice: Subject to any disclaimer, the term of this patent is extended or adjusted under 35 U.S.C. 154(b) by 108 days.

(21) Appl. No.: 16/627,248

(22) PCT Filed: Jul. 5, 2018

(86) PCT No.: PCT/US2018/040882
§ 371 (c)(1),
(2) Date: Dec. 27, 2019

(87) PCT Pub. No.: WO2019/010281
PCT Pub. Date: Jan. 10, 2019

(65) Prior Publication Data
US 2020/0164007 A1 May 28, 2020

Related U.S. Application Data

(60) Provisional application No. 62/529,733, filed on Jul. 7, 2017.

(51) Int. Cl.
*A61K 35/747* (2015.01)
*A61P 31/04* (2006.01)
*A61K 45/06* (2006.01)
*A61P 15/02* (2006.01)
*A61P 15/08* (2006.01)
*A61K 9/00* (2006.01)

(52) U.S. Cl.
CPC .......... *A61K 35/747* (2013.01); *A61K 9/0034* (2013.01); *A61K 45/06* (2013.01); *A61P 15/02* (2018.01); *A61P 15/08* (2018.01); *A61P 31/04* (2018.01)

(58) Field of Classification Search
None
See application file for complete search history.

(56) References Cited

U.S. PATENT DOCUMENTS

| 10,398,742 | B2 * | 9/2019 | Ensign | A61K 9/0095 |
| 10,918,663 | B2 * | 2/2021 | Richards | A61P 31/22 |
| 11,083,761 | B2 * | 8/2021 | Parks | A61K 47/26 |
| 2010/0151026 | A1 | 6/2010 | Liu et al. | |
| 2011/0066137 | A1 | 3/2011 | Parks et al. | |
| 2020/0164007 | A1 * | 5/2020 | Parks | A61P 15/08 |
| 2020/0171107 | A1 * | 6/2020 | Parks | A61K 35/747 |
| 2020/0230183 | A1 * | 7/2020 | Parks | C12N 1/04 |
| 2021/0330721 | A1 * | 10/2021 | Parks | C12N 1/04 |

FOREIGN PATENT DOCUMENTS

| EP | 2037938 A2 * | 3/2009 | ......... A61K 31/7056 |
| EP | 3648778 A1 * | 5/2020 | ............. A61P 31/04 |
| WO | 9846261 A1 | 10/1998 | |
| WO | WO-2008007098 A2 * | 1/2008 | ............. A61P 31/04 |
| WO | WO-2018045359 A1 * | 3/2018 | ............. C12Q 1/701 |
| WO | WO-2019010281 A1 * | 1/2019 | ......... A61K 31/4164 |
| WO | WO-2019010282 A1 * | 1/2019 | ........... A61K 9/0034 |
| WO | WO-2019224012 A1 * | 11/2019 | ......... G01N 33/6893 |
| WO | WO-2020007780 A1 * | 1/2020 | ............. A61P 15/08 |
| WO | WO-2020047203 A2 * | 3/2020 | ......... A61K 31/4168 |

OTHER PUBLICATIONS

Haahr et al, BMJ Open, 2020 10:e035866 (Year: 2020).*
Haahr et al, Journal of Infectious Diseases. 2019, 219:1809-17, published online Dec. 29, 2018 (Year: 2019).*
Nilsen et al, Applied and Environmental Microbiology, 2020, 86:e01594-20. published: Oct. 1, 2020 (Year: 2020).*
Schmitt et al, British Infection Association, 2014. 69:123-133, available online: May 9, 2014 (Year: 2014).*
Catania et al, Biochimica Clinica, 2018, 42/Supplement 1, pp. S174. Abstract No. P284. Abstract only (Year: 2018).*
"Clinical Trials Register", Anonymous, Available Online at: https://www.clinicaltrialsregister.eu/ctr-search/trial/2016-002385-31/DK, Nov. 7, 2016, 5 pages.
Hemmerling et al., "Phase 2a Study 14 Assessing Colonization Efficiency, Safety, and Acceptability of *Lactobacillus crispatus* CTV-05 in Women With Bacterial Vaginosis", Sexually Transmitted Diseases, vol. 37, No. 12, XP055470324, Dec. 1, 2010, pp. 745-750.
EP18828806.2, "Extended European Search Report", dated Feb. 16, 2021, 14 pages.
Haahr, T et al., "Treatment of Abnormal Vaginal Microbiota before Frozen Embryo Transfer: Case-Report and Minireview to Discuss the Longitudinal Treatment Efficacy of Oral Clindamycin.," Frontiers in Physiology., Jun. 19, 2017, vol. 8, No. 415; pp. 1-6.

(Continued)

Primary Examiner — Nita M. Minnifield
(74) Attorney, Agent, or Firm — Kilpatrick Townsend & Stockton LLP

(57) ABSTRACT

This invention provides for a method for improving the success rate of in vitro fertilization in women hosting abnormal vaginal microbiota. The method comprises the steps of: (i) selecting a woman suspected of hosting abnormal vaginal microbiota (AVM); (ii) administering to the woman a suitable antibiotic administered in an amount and duration effective to reduce the quantity of abnormal vaginal microbiota hosted by the woman; (iii) administering to the woman via vaginal administration an amount of *Lactobacillus* species in an amount sufficient to colonize the vaginal mucosa; and, (iv) transferring an embryo to the woman.

13 Claims, 4 Drawing Sheets

(56) References Cited

OTHER PUBLICATIONS

Sirota, I et al., "Potential Influence of the Microbiome on Infertility and Assisted Reproductive Technology," Seminars in Reproductive Medicine. Jan. 2014, Epub Jan. 3, 2014, vol. 32, No. 1; pp. 1-16.
International Search Report and Written Opinion in PCT/US18/40882, dated Sep. 18, 2018.

* cited by examiner

USE OF VAGINAL *LACTOBACILLI* FOR IMPROVING THE SUCCESS RATE OF IN VITRO FERTILIZATION

CROSS-REFERENCES TO RELATED APPLICATIONS

The present application is a U.S. National Phase of PCT/US2018/040882, International Filing Date Jul. 5, 2018, which claims priority to U.S. Provisional Pat. Appl. No. 62/529,733, filed on Jul. 7, 2017, the entire content of which is incorporated in its entirety herein for all purposes.

BACKGROUND OF THE INVENTION

Generally, healthy vaginal microbiota is dominated by *Lactobacillus* species, which are gram positive rods that play an important role in resisting infection via production of lactic acid and acidification of the vagina, or by production of other antimicrobial products, such as hydrogen peroxide ($H_2O_2$). The species of *Lactobacillus* most commonly isolated from the reproductive tracts of women worldwide include *L. crispatus, L. jensenii, L. gasseri*, and *L. iners*. See, e.g., Antonio et al., (1999) *J. Infect. Dis.* 180:1950-1956; Vasquez et al., (2002) *J. Clin. Microbiol.* 40:2746-2749; Vallor, A. C., et al. *J Infect Dis.* 2001 Dec. 1, 184(11):1431-6; Ravel, J., et al. *Proc Natl Acad Sci, USA.* 2011 Mar. 15, 108 Suppl 1:4680-7. *L. crispatus, L. jensenii*, and *L. gasseri* are capable of producing $H_2O_2$, whereas *L. iners* strains generally do not produce $H_2O_2$. These species are phylogenetically and functionally different from food and/or environmental *Lactobacillus* species. These facultative anaerobes metabolize glucose to lactic acid, contributing to the maintenance of a low vaginal pH (4.0-4.5) that accounts for a major part of the non-specific host defense of the vagina. The $H_2O_2$-producing strains (e.g. *L. crispatus* and *L. jensenii*) are more protective than those that do not produce $H_2O_2$ (*L. iners*). Indeed, it has been demonstrated that women with predominant vaginal *Lactobacillus* microbiota have a 50% lower frequency of gonorrhea, chlamydial infections, trichomoniasis and bacterial vaginosis. Therefore, beneficial lactobacilli associated with normal vaginal microbiota can be considered to provide a protective "biofilm." See, e.g., Falagas et al., (2006) *Drugs,* 66:1253-1261.

In most healthy women of child-bearing age, the vaginal microbiota exhibits low microbial diversity and is dominated by $10^7$-$10^9$ colony forming units (CFU) of *Lactobacillus* per gram of fluid, while the vagina is acidic and contains low levels of proinflammatory cytokines. Unfortunately, some women of childbearing age lack or have low levels of vaginal *Lactobacillus*, which can be due to the fact that the vaginal microbial ecosystem is dynamic and can be affected by the menstrual cycle, medications, general health status, sexual and hygiene practices, and contraception. Loss of the dominant vaginal *Lactobacillus* species leads to a more diverse abnormal microbiota populated with facultative and strict anaerobes, such as *Gardnerella vaginalis* and *Atopobium vaginae*, higher vaginal pH, and higher levels of proinflammatory cytokines (i.e., bacterial vaginosis).

BV is typically diagnosed using the Amsel's critera which include the symptoms such as homogeneous, white vaginal discharge having a fishy odor and a pH>4.5 and the presence of clue-cells (squamous epithelial cells covered with adherent bacteria), or the Nugent score, based on a Gram-stained vaginal smear (Amsel, R. et al. (1983) *Am. J. Med.* 74:14-22 and Nugent, R. P. et al. (1991) *J. Clin. Microbiol.* 29:297-301). However, not all women show symptoms of BV. In fact, one recent study indicated that up to 50% of BV cases are asymptomatic (Ravel, J. et al. (2013) *Proc. Natl. Acad. Sci. USA* 108 Suppl 1:4680-4687).

Lower genital tract infections involving the presence of abnormal vaginal microbiota, including sexually transmitted diseases (STDs), are some of the most common clinical problems among women of childbearing age. Abnormal vaginal microbiota, specifically bacterial vaginosis (BV), is one of the most common genital infections in pregnancy. The presence of abnormal vaginal microbiota during pregnancy is linked to preterm delivery, low birth weight, and neonatal mortality. Women with bacterial vaginosis diagnosed during the second trimester of pregnancy are 40 percent more likely to give birth to a premature, low-birth weight infant than women without bacterial vaginosis. See, e.g., Hay, P. E. et al. (1994) *BMJ.* 308:295-298; Hillier, S. L. et al. (1995) *N. Engl. J. Med.* 333:1737-1742; Larsson, P. G. et al. (2000) *Acta. Obstet. Gynecol. Scand.* 79:390-396; Svare, J. A. et al. (2006) *BJOG* 113:1419-1425; Thorsen, P. et al. (2006) *Acta. Obstet. Gynecol. Scand.* 85:906-911; and Brocklehurst, P. et al. (2013) *Cochrane Database Syst. Rev.* 1: CD000262.

Furthermore, bacterial vaginosis has also been found in approximately 19% of the infertile female population. See, e.g., Haahr, T. et al. *Hum. Reprod.* 2016 Apr., 31(4):795-803. The BV studies conducted in infertile women suggest that the presence of AVM impacts female fertility and is negatively correlated with the clinical pregnancy rate in IVF patients (Haahr, T. et al. *Hum. Reprod.* 2016 Apr., 31(4): 795-803; Mangot-Bertrand, J. et al (2013) *Microbia Infect. Dis.* 32:535-541; Salah, R. M. et al. (2013) *Eur. J. Obstet. Gynecol. Reprod. Biol.* 167:59-63). The present invention addresses these and other needs in the context of IVF procedures.

BRIEF SUMMARY OF THE INVENTION

In one aspect, the present invention provides for a method for improving the success rate of in vitro fertilization in women hosting abnormal vaginal microbiota. The method involves (i) selecting a woman suspected of hosting abnormal vaginal microbiota (AVM); (ii) administering to the woman an antibiotic active against bacterial vaginosis associated bacteria (e.g., *Gardnerella vaginalis* and *Atopobium vaginae*) for at least 5 days prior to step iii, wherein said antibiotic is administered in an amount and duration effective to reduce the quantity of abnormal vaginal microbiota hosted by the woman; (iii) administering to the woman via vaginal administration an amount of *Lactobacillus* species, wherein the amount of *Lactobacillus* is sufficient to colonize the vaginal mucosa following the antibiotic administration of step ii, wherein the *Lactobacillus* species is selected from a group of species consisting of: *Lactobacillus crispatus, Lactobacillus jensenii* and *Lactobacillus gasseri*, wherein said species have the ability to produce greater than 0.5 ppm of hydrogen peroxide under effective culture conditions; and, (iv) transferring a human zygote or embryo to the woman.

In some embodiments, the method for improving the success rate of in vitro fertilization in women hosting abnormal vaginal microbiota involves the administration of the amount of *Lactobacillus* daily at between $10^8$ to $10^{10}$ CFU per dose. In some embodiments, the method for improving the success rate of in vitro fertilization in women hosting abnormal vaginal microbiota involves the administration of either clindamycin as the antibiotic or metronidazole as the antibiotic. In another embodiment, the patient has

*Gardnerella vaginalis* and/or *Atopobium vaginae* levels above the accepted thresholds defining AVM. In another embodiment, the *Lactobacillus* species is administered to the patient once daily for 7 days at between $10^8$ to $10^{10}$ CFU per dose prior to embryo transfer (ET), followed by twice weekly at the same dose for 7 weeks until clinical pregnancy is determined by ultrasound and/or detection of a fetal heartbeat.

In some embodiments, the method for improving the success rate of in vitro fertilization in women hosting abnormal vaginal microbiota involves the administration of the *Lactobacillus* as a dry composition. In some embodiments, the *Lactobacillus* is suspended, prior to drying, in an aqueous preservation medium. In some embodiments, the aqueous preservation medium can be comprised of trehalose at between 5-15% (w/v), xylitol at between 2-7% (w/v), sodium ascorbate at between 0.5-1.0% (w/v), sodium phosphate at between 10-30 mM, and, optionally, sodium glutamate at between 0-5% (w/v).

In some embodiments of the invention, the method for improving the success rate of in vitro fertilization in women hosting abnormal vaginal microbiota involves the co-administration of the *Lactobacillus* species with the antibiotic. In some embodiments, the *Lactobacillus* species is administered after completion of the antibiotic treatment of step ii. In another embodiment of the methods described herein, the *Lactobacillus* species is administered at least 7 days prior embryo transfer. In some embodiments, the preferred species of *Lactobacillus* is *L. crispatus*, and it may be administered alone or in combination with at least one more species of *Lactobacillus*.

In an aspect the invention relates to a composition comprising an amount of *Lactobacillus* species for use in the treatment of a woman suffering from or is suspected of suffering from abnormal vaginal microbiota (AVM) and is expected to receive IVF (and/or having a human zygote or embryo transferred) after said treatment, wherein said woman has previously been treated with an antibiotic active against bacterial vaginosis associated bacteria, including *Gardnerella vaginalis* and *Atopobioum vaginae* (for e.g. at least 5 days), wherein said antibiotic has been administered in an amount and duration effective to reduce the quantity of abnormal vaginal microbiota hosted by said woman; wherein said composition is for vaginal administration.

Another aspect of the invention relates to a kit of parts for use in the treatment of abnormal vaginal microbiota and/or for use in improving the success rate of in vitro fertilization in women hosting or suspected of hosting abnormal vaginal microbiota, said kit of parts comprising: a first container comprising one or more antibiotics active against bacterial vaginosis associated bacteria, including *Gardnerella vaginalis* and *Atopobioum vaginae*; a second container comprising an amount of *Lactobacillus* species; and optionally, instructions for use of said kit in the treatment of abnormal vaginal microbiota and/or for use in improving the success rate of in vitro fertilization in women hosting or suspected of hosting abnormal vaginal microbiota.

In a preferred embodiment, said one or more antibiotics are for administration for e.g. at least 5 days to said woman before administration of said *Lactobacillus* species, and said antibiotics are for administration in an amount and duration effective to reduce the quantity of abnormal vaginal microbiota hosted by said woman; and wherein said *Lactobacillus* species are for vaginal administration in an sufficient amount to colonize the vaginal mucosa following the antibiotic administration.

Thus, the kit of part are preferably intended for sequential administration of i) the antibiotics followed by ii) the *Lactobacillus* species, for use in the treatment of abnormal vaginal microbiota and/or for use in improving the success rate of in vitro fertilization in women hosting or suspected of hosting abnormal vaginal microbiota. Thus, after the treatment the woman may have improved success rate of in vitro fertilization.

In an embodiment, the amount of *Lactobacillus* is sufficient to colonize the vaginal mucosa following the antibiotic treatment, wherein the *Lactobacillus* species is e.g. selected from a group of species consisting of: *Lactobacillus crispatus, Lactobacillus jensenii* and *Lactobacillus gasseri*, wherein said species have the ability to produce greater than 0.5 ppm of hydrogen peroxide under effective culture conditions.

It should be noted that embodiments and features described in the context of one of the aspects of the present invention also apply to the other aspects of the invention. As such, it should be understood that any and all aspects encompassed by dependent claims 2-13 can also apply to independent claim 14.

DETAILED DESCRIPTION OF THE INVENTION

I. Introduction

Figure 1:
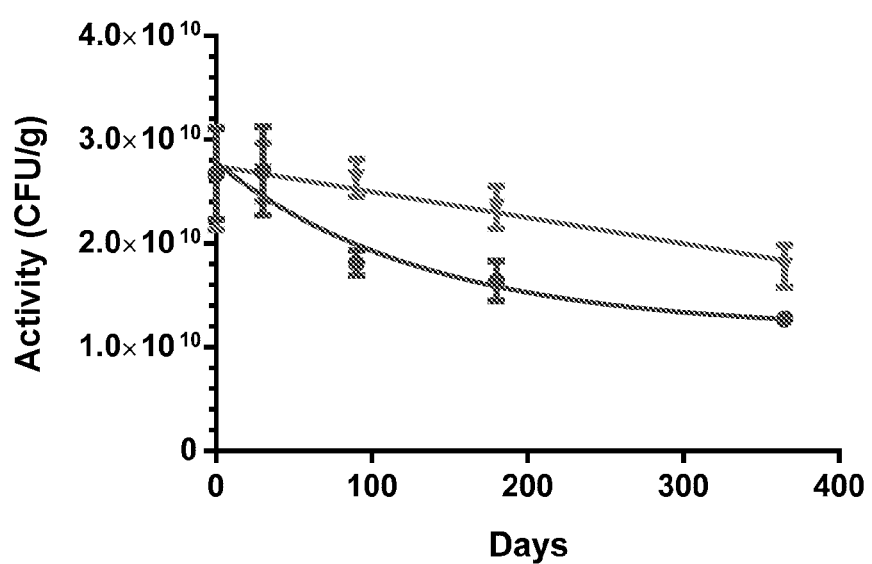
FIG. 1. Stability of LACTIN-V formulated with skim milk (lower line, circles) or without skim milk (upper line, triangles). Powder samples were stored at 25° C. and activity determined at different time points by culturing on MRS agar plates and counting colonies.

This invention provides for a method of improving the success rate of in vitro fertilization in women hosting abnormal vaginal microbiota by administering a treatment regimen of an antibiotic and a high potency formulation of *Lactobacillus* prior to transferring an embryo to the woman. The high potency *Lactobacillus* formulation is suitable for administration to a woman as a treatment where the formulation has high colonization potency and no animal-derived excipients. Specifically, as disclosed herein, the present invention provides methods for replacing the bacteria associated with abnormal vaginal microbiota (e.g., *Gardnerella vaginalis* and/or *Atopobium vaginae*) with *Lactobacillus*, repopulating the vaginal mucosa with protective bacteria associated with normal vaginal microbiota as a means to increase the success rate of in vitro fertilization in women. As described in more detail below, the present invention teaches methods and use of antibiotics and *Lactobacillus* formulations for IVF.

II. Definitions

As used herein, the terms "in vitro fertilization" or "IVF" refer to a method of fertilizing an egg outside of a living human. IVF is a process by which an egg is fertilized by sperm outside the body (i.e., in vitro, which literally translates to "in glass" but is understood in the art to refer to processes performed, for example, in a laboratory or other artificial setting). In some embodiments, an IVF process may involve monitoring and/or stimulating a female's ovulatory process, removing oocyte or oocytes (egg or eggs) from a female's ovaries, and/or contacting sperm and oocytes with one another in a laboratory (e.g., in a fluid medium) to achieve fertilization. In some embodiments, IVF involves culturing a fertilized egg (zygote) in a growth medium and/or either implanting it in a female's uterus or storing it for future analysis and/or implantation. In some embodiments, IVF may involve sorting fertilized eggs for particular desired attributes (e.g., gender).

As used herein, the terms "abnormal vaginal microbiota" or "AVM" or "abnormal vaginal microbiome" or "vaginal dysbiosis" refer to a condition in which the vaginal mucosa lacks a sufficient amount of protective *Lactobacillus* species and is colonized by significant numbers of diverse non-*Lactobacillus* species. Examples of non-*Lactobacillus* species associated with abnormal vaginal microbiota, specifically bacterial vaginosis (BV), include, but are not limited to, *Gardnerella vaginalis* and *Atopobium vaginae*. The condition can be symptomatic or asymptomatic. The terms "vaginal microbiota" or "vaginal microbiome" are used interchangeably and refer to the microorganisms that colonize the vagina, although "microbiota" and "microbiome" are the preferred terms.

As used herein, the term "AVM threshold level" refers to the standardized amount of *G. vaginalis* and/or *A. vaginae* used to diagnostically determine the health of the vaginal microbiome of a woman. A sample with a *G. vaginalis* and/or *A. vaginae* bacterial load below the determined threshold is determined negative for AVM; a sample with a *G. vaginalis* and/or *A. vaginae* bacterial load above the determined threshold is determined positive for AVM. The AVM threshold levels are determined by quantitative PCR (qPCR) and ROC curve analysis, the methods of which are described in detail below.

As used herein, the term "antibiotic" refers to any chemotherapeutic agent (e.g., an agent produced by microorganisms and/or synthetically) that has the capacity to inhibit the growth of and/or to kill, one or more microorganisms (e.g., bacteria, fungi, parasites and the like) or aberrantly growing cells (e.g., tumor cells). As used herein, antibiotics are well-known to those of skill in the art. Classes of antibiotics include, but are not limited to, aminoglycosides (e.g., amikacin, gentamicin, kanamycin, neomycin, netilmicin, streptomycin, tobramycin, paromomycin and the like), ansamycins (e.g., geldanamycin, herbimycin and the like), carbacephem (e.g., loracarbef), carbapenems (e.g., ertapenem, doripenem, imipenem/cilastatin, meropenem and the like) cephalosporins (e.g., first generation (e.g., cefadroxil, cefazolin, cefalotin, cefalexin and the like), second generation (e.g., cefaclor, cefamandole, cefoxitin, cefprozil, cefuroxime and the like), third generation (e.g., cefixime, cefdinir, cefditoren, cefoperazone, cefotaxime, cefpodoxime, ceftazidime, ceftibuten, ceftizoxime, ceftriaxone and the like), fourth generation (e.g., cefepime and the like) and fifth generation (e.g., ceftobiprole and the like)), glycopeptides (e.g., teicoplanin, vancomycin and the like), macrolides (e.g., azithromycin, clarithromycin, dirithromycin, erythromycin, roxithromycin, troleandomycin, telithromycin, spectinomycin and the like), monobatams (e.g., aztreonam and the like), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticacillin and the like), polypeptides (e.g., bacitracin, colistin, polymyxin B and the like) quinolones (e.g., ciprofloxacin, enoxacin, gatifloxacin, levofloxacin, lomefloxacin, moxifloxacin, norfloxacin, ofloxacin, trovafloxacin and the like), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines (e.g., demeclocycline, doxycycline, minocycline, oxytetracycline, tetracycline and the like) and others (e.g., arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, tinidazol and the like) (See, e.g., Robert Berkow (ed.) *The Merck Manual of Medical Information—Home Edition*. Pocket (September 1999), ISBN 0-671-02727-1). Clindamycin, metronidazole and tinidazole are examples of antibiotics which are particularly active against *Gardnerella vaginalis* and *Atopobium vaginae*.

As used herein, the term "*Lactobacillus*" refers to bacteria that are Gram-positive facultative anaerobic bacteria, characterized by the ability to produce lactate (lactic acid) from carbohydrate sources such as glucose. These bacteria may be present in food products or be commensal organisms that colonize the vaginal or gastrointestinal mucosa.

As used herein, the terms "*Lactobacillus crispatus*" or "*L. crispatus*" refer to a species of the *Lactobacillus* genus. The species is generally distinguished from other lactobacilli based on the polynucleotide sequence of the ribosomal 16S ribosomal RNA gene. "*Lactobacillus gasseri*" or "*L. gasseri*" and "*Lactobacillus jensenii*" or "*L. jensenii*" refer to other species of *Lactobacillus*. *L. crispatus*, *L. gasseri*, *L. jensenii* are vaginal species capable of producing hydrogen peroxide.

As used herein, the term "amount sufficient to colonize" refers to an amount of *Lactobacillus* species which establishes the presence of a healthy, viable reproducing microbial population of *Lactobacillus* on vaginal mucosa.

As used herein, the term "effective culture conditions" refers to the in vitro environment in which *Lactobacillus* cells are placed in or are exposed to in order to promote growth of said cells. Thus, the term refers to the medium, temperature, atmospheric conditions, substrate, stirring conditions and the like which may affect the growth of cells permitting a generation time (doubling rate of cell population) of about 0.5 to 2.5 hours.

As used herein, the terms "embryo transfer" and "zygote transfer" refer to the process of introducing an in vitro fertilized egg or embryo into a woman's uterus.

As used herein, the term "pregnancy scan" refers to the assessment of the woman into which an embryo or zygote has been transferred using any variety of techniques known in the art. A "biochemical pregnancy scan" is the assessment of the urine and/or blood levels of human chorionic gonadotropin (hCG) in a woman into which an embryo or zygote has been transferred. Detection of hCG levels above a certain threshold (e.g., at least 25 mtU/mL (milli-international units per milliter)) at a certain time point after embryo transfer (e.g., 3 or 4 weeks) are indicative of a biochemically detectable pregnancy. A "clinical pregnancy scan" is the assessment of the woman into which an embryo or zygote has been transferred using an ultrasound scan or Doppler testing. The presence of a gestational sac and/or heart motion on ultrasound or Doppler testing indicates implantation and a clinical pregnancy.

As used herein, the term "implantation" refers to the event after fertilization of a human ovum wherein the resultant human embryo, at this stage a blastocyte, adheres to the uterine wall.

As used herein, the term "dry composition" refers to a composition from which moisture has been removed. Drying or desiccation techniques include, e.g., heating (e.g., sublimation), application of low pressure or vacuum, lyophilization (i.e., freeze drying), and combinations thereof. Compositions are commonly desiccated for easy storage and transport.

As used herein, the term "lyophilization" refers to the process of freezing a substance and then reducing the concentration of water, by sublimation and/or evaporation to levels which do not support biological or chemical reactions.

As used herein, the term "animal-derived components" refers to inert substances derived from an animal, which may be included in a composition comprised of substances that are considered active ingredients. Non-limiting examples include milk, yogurt, butter oil, chicken fat, lard, gelatin, and tallow.

As used herein, the terms "aqueous preservation medium" or "preservation formulation" or "preservation medium" are used interchangeably and refer to a composition capable of preserving and maintaining a bacterial culture in a metabolically inactive state while minimizing the damaging effects encountered during the preservation process. Generally, a *Lactobacillus* strain is converted from an actively growing metabolic state to a metabolically inactive state upon addition to the preservation medium, freezing and lyophilization. The preservation medium can therefore be formulated for optimal cell resilience, such that the cells can adhere to mucosal surfaces upon rehydration and return to full metabolic activity. The aqueous preservation medium includes, for example, a carbohydrate, a polyol (sugar alcohol), an anti-oxidant, a buffering agent, and, optionally, an amino acid. The aqueous preservation medium is used to resuspend a cell pellet of bacteria to a concentration of about $10^{10}$ CFU/mL, where the suspension can be dried, stored for at least 2 years at 2-8° C., and resuspended with a loss of CFU of less than 15%.

As used herein, the term "excipient" and "inactive excipient" are used interchangeably and refer to inert substances formulated alongside the active ingredient of a medication, included for the purpose of long-term stabilization, dilution, providing bulk to the powder formulation (thus often referred to as "bulking agents," "fillers," or "diluents"), or to confer a therapeutic enhancement on the active ingredient in the final dosage form, such as facilitating drug absorption, reducing viscosity, or enhancing solubility. Examples of excipients include, without limitation, cellulose, ethylcellulose, cellulose acetate, sodium carboxymethylcellulose, methylcellulose, hydroxypropyl methylcellulose, microcrystalline cellulose, sodium alginate, polyvinylpyrrolidone (i.e., crospovidone), croscarmellose sodium, gum tragacanth, powdered tragancanth, gum acacia, polyoxyethylene stearate, heptadecaethylene oxycetanol, polyoxyethylene sorbitol monooleate, polyethylene sorbitan monooleate, lactose, glucose, sucrose, trehalose, maltodextrin, Pharmasperse®, pre-gelatinized starch, malt, talc, colloidal silica, stearic acid, magnesium stearate, sodium stearyl fumerate, dibasic calcium phosphate, calcium sulfate, peanut oils, cotton seed oil, sesame oil, olive oil, corn oil and, propylene glycol, glycerine, sorbitol, mannitol, xylitol, polyethylene glycol, agar, alginic acids, pyrogen-free water, isotonic saline, phosphate buffer solution, or a combination thereof.

III. Methods

Diagnosing Women with Abnormal Vaginal Microbiota (AVM)

Abnormal vaginal microbiota can be detected and diagnosed using any suitable means known in the art. AVM can be symptomatic or asymptomatic. Symptoms generally include abnormal odor and/or discharge, and discomfort from itching and/or pain. Depending on the vaginal infection, it can be detected by a woman without medical consultation using over the counter diagnostic apparatuses or kits.

In some cases, medical practitioners will detect and diagnose the AVM. Clinical criteria require the presence of at least three symptoms, including those mentioned above, a vaginal fluid pH of >4.5, and the presence of clue cells (e.g., vaginal epithelial cells studded with adherent coccobacilli) on microscopic examination. The medical practitioner will obtain swabs from the posterior fornix during speculum examination to test for AVM. For example, bacterial vaginosis can be detected, e.g., by Amsel clinical criteria or Gram stained vaginal smears (Nugent scoring system). The Gram stained vaginal smear is used to determine the relative concentrations of lactobacilli (Gram-positive bacteria), Gram-negative and Gram-variable rods and cocci (i.e., *Gardnerella vaginalis, Atopobium vaginae, Prevotella, Porphyromonas*, and peptostreptococci), and curved Gram-negative rods (i.e., *Mobiluncus*) characteristic of BV. Detection and diagnostic methods for symptomatic abnormal vaginal microbiota are well known in the art and are described in U.S. Pat. No. 8,329,447. See also, Haahr, T. et al. *Hum. Reprod.* 2016 April, 31(4):795-803; Datcu, R. et al. *BMC Infectious Diseases* 2013, 13:480; https://www.cdc.gov/std/tg2015/bv.htm.

In some cases, a woman suspected of hosting abnormal vaginal microbiota can have asymptomatic AVM. Quantitative Polymerase Chain Reaction (qPCR) methods can be used to diagnose a woman with AVM having no symptoms. For example, a woman having no symptoms can be tested for BV by a medical practitioner using qPCR to identify and quantify specific bacteria of the vaginal microbiome. The medical practitioner can extract bacterial DNA from vaginal samples using a commercially available DNA isolation kit, such as, for example, Fast DNA™ SPIN kit for Soil (MP Biomedicals, Santa Ana, Calif., USA) and perform qPCR with a suitable amount of template DNA.

Positive controls and specificity controls for the bacteria of interest (i.e., *Gardnerella vaginalis* and *Atopobium vaginae*) are obtained by DNA extraction from culture collection strains using standard protocols described in the art. The controls are used to determine the AVM threshold by receiver operating characteristic (ROC) curve analysis and the bacterial communities are molecularly defined based on qPCR results. The thresholds are ultimately defined by the ROC curve analysis using Nugent BV scoring as the gold standard. Nugent scores of 7-10 are used to define BV as reference standard by correlating Nugent BV standards to their qPCR results. The current threshold levels for *G. vaginalis* and *A. vaginae* are established as $5.7 \times 10^7$ and $5.7 \times 10^6$ 16S rRNA gene copies/mL, respectively. The samples collected from a woman with a bacterial load which are above the cut-off points (i.e., as defined by the ROC) are considered positive for AVM and the samples with a bacterial load below the cut-off points are considered negative for AVM. Detection and diagnostic methods for asymptomatic abnormal vaginal microbiota are described in detail in Haahr, T. et al. *Hum. Reprod.* 2016 April, 31(4):795-803 and Datcu, R. et al. *BMC Infectious Diseases* 2013, 13:480. A woman diagnosed with AVM using any of the above described diagnostic methods will be administered antibiotics as described below.

Administration of Antibiotics

A woman diagnosed with abnormal vaginal microbiota can be administered an antibiotic active against *Gardnerella vaginalis* and *Atopobium vaginae*. The antibiotic can be administered in any suitable amount and suitable duration to reduce the quantity of the AVM. Suitable antibiotics for the reduction of abnormal vaginal microbiota (i.e., *Gardnerella vaginalis* and *Atopobium vaginae*) are well known in the art. Such antibiotics include, but are not limited to, clindamycin, metronidazole, and tinidazole. Antibiotics can be administered individually or as a combination therapy.

The antibiotic for use in the reduction of AVM in a woman can be in any suitable form for administration. For example, the antibiotic can be delivered topically (as a gel or cream), or as an oral or vaginal tablet, capsule or suppository. In a particular embodiment, the antibiotic is administered as an oral capsule or a topical gel. In some embodiments, the antibiotic is administered as an oral tablet. In some embodiments, the antibiotic is administered as a topical gel.

The antibiotic treatment can be administered 1 or 2 times per day. In some embodiments of the invention, the antibiotic can be administered for between 2 and 7 days. In other embodiments, the antibiotic can be administered for 2, 3, 4, 5, 6, and 7 days. In some other embodiments, the antibiotic can be administered for between 2 and 7 days, or 3 and 6 days, or 4 and 5 days, or 4 and 7 days. In particular embodiments, the antibiotic can be administered for between 2 and 7 days. In another embodiment, the antibiotic can be administered for 7 days. In another embodiment, the antibiotic can be administered for 5 days.

The antibiotic can be administered in any suitable dosage effective to reduce the quantity of abnormal vaginal microbiota hosted by a woman. The antibiotic treatment is administered as an oral capsule in a dosage from about 0.1 mg to about 10,000 mg, or about 1 mg to about 1000 mg, or about 10 mg to about 750 mg, or about 25 mg to about 500 mg, or about 50 mg to about 250 mg. Suitable dosages for the antibiotic oral tablet include about 1 mg, 5, 10, 20, 30, 40, 50, 60, 70, 80, 90, 100, 200, 300, 400, 500, 600, 700, 800, 900 or 1200 mg. In some embodiments, the dose of the antibiotic oral tablet is between about 200 mg and 300 mg.

In some embodiments, the dosage of an antibiotic oral tablet can be about 0.1 mg/kg of body weight per patient, or 0.5, 1, 5, 10, 25, 50, 100, 250, 500, 750, or 1000 mg/kg of body weight per patient. In other embodiments, the dosage of an antibiotic oral tablet can be from about 0.1 to 1000 mg/kg of body weight per patient, or from about 0.5 to 750, or from about 1 to 500, or from about 5 to 250, or from about 10 to 100, or from about 25 to 50 mg/kg of body weight per patient. In still another embodiment, the dosage can be between about 0.5 to about 25 mg/kg of body weight per patient, or between about 5 to 15 mg/kg of body weight per patient, or between about 8 to about 12 mg/kg of body weight per patient, or about 10 mg/kg of body weight per patient.

In some embodiments, the antibiotic treatment is administered as a topical gel in a dosage from about 0.1% to about 2% of the total gel formulation, or about 0.3% to about 1.75%, or about 0.5% to about 1.25%, or about 0.75% to about 1%. Suitable dosages for the antibiotic topical gel include about 0.1%, 0.2, 0.3, 0.4, 0.5, 0.6, 0.7, 0.8, 1.0, 1.1, 1.2, 1.3, 1.4, 1.5, 1.6, 1.7, 1.8, 1.9 or 2%. In some embodiments, the dose of the antibiotic topical gel is about 0.75%. In other embodiments, the dose of the antibiotic topical gel is about 1.0%. Upon completion of the antibiotic treatment regimen as described above and reduction in abnormal vaginal microbiota, the woman will be administered *Lactobacillus* as described below.

*Lactobacillus* Species

As explained herein, women hosting AVM and having received an antibiotic treatment regimen as described above are administered a suitable *Lactobacillus* species in an amount sufficient to colonize or populate the vaginal mucosa. The *Lactobacillus* species suitable for use in the present invention can be any $H_2O_2$-producing *Lactobacillus* species that has the identifying characteristics described herein. *Lactobacillus* strains can be detected and isolated from natural sources using appropriate screening techniques that are known in the art. Specifically, suitable strains of *Lactobacillus* for use in a medicant of the present invention can be obtained through publicly available resources, such as American Type Culture Collection (ATCC) or Biodefense and Emerging Infections Research Resources Repository (BEI, beiresources.org) or isolated from the healthy vagina of a human. The identifying characteristics of *Lactobacillus* strains suitable for use in the present invention and methods to screen for these characteristics are discussed in detail below.

One identifying characteristic of a *Lactobacillus* suitable for use in the present invention is that the *Lactobacillus* strain has a percent vaginal epithelial cell (VEC) cohesion value of at least about 50%. A "percent VEC cohesion value" is defined as the percentage of VECs to which at least one *Lactobacillus* cell is adhered in the total number of VECs in an identified group. Methods used to determine acceptable VEC cohesion values are well known in the art and can be found in U.S. Pat. Nos. 6,468,526 and 6,093,394. See also Kwok, et al., *J. Urol.* 2006, 176:2050-2054. Another identifying characteristic of a *Lactobacillus* which is suitable for the present invention is the ability to produce hydrogen peroxide ($H_2O_2$). The $H_2O_2$ positive phenotype is also associated with sustained vaginal colonization. See, e.g., Vallor, A. C., et al., *J Infect Dis.* 2001 Dec. 1; 184(11):1431-6. Preferably, the *Lactobacillus* can produce greater than about 0.5 ppm of $H_2O_2$ under normal growth conditions. More preferably, the *Lactobacillus* can produce at least about 10 ppm of $H_2O_2$, and even more preferably, the *Lactobacillus* can produce at least about 20 ppm of $H_2O_2$ under effective growth conditions, herein defined as any medium and conditions capable of promoting production of $H_2O_2$. Hydrogen peroxide producing vaginal *Lactobacillus* include most *L. crispatus* and *L. jensenii* strains, and approximately half of *L. gasseri* strains, as described in Antonio et al. *The Journal of Infectious Diseases* 1999, 180:1950-6.

Another identifying characteristic of a *Lactobacillus* suitable for use in the present invention is the genetic identity and stability of the *Lactobacillus* strain over time both in vivo and in vitro. Repetitive Sequence Polymerase Chain Reaction (Rep-PCR) can be used to confirm genetic identity and stability of a strain of *Lactobacillus* over time after either in vitro storage or in vivo colonization of vaginal epithelial cells. Rep-PCR methods used to confirm genetic identity of *Lactobacillus* strains are well known in the art and can be found in U.S. Pat. No. 6,093,394. See also, Antonio & Hillier, *J Clin. Microbiol.* 2003, 41: 1881-1887.

Another identifying characteristic of a *Lactobacillus* suitable for use in the present invention is the ability to produce lactic acid. Lactic acid has been shown to inhibit the growth of pathogens in vitro. Preferably, a *Lactobacillus* produces at least about 0.75 mg/100 mL lactic acid, and more preferably at least about 4 mg/100 mL lactic acid, and even more preferably at least about 8.8 mg/100 mL lactic acid under effective growth conditions. A suitable *Lactobacillus* strain can have a relatively large cell size. As provided in Bergey's Manual of Determinative Bacteriology, typical *Lactobacillus* are 0.8-1.6 μm in width and 2.3-11 μm in length. A preferred *Lactobacillus* strain for use in the present invention has a cell size of from about 1 to about 2 microns in width and from about 2 to about 4 microns in length.

In addition to known species and strains of *Lactobacillus*, newly identified species and strains from nature and mutant strains derived from known or newly identified strains can be used in a medicant of the present invention. Mutants of a parental strain of *Lactobacillus* that have the identifying characteristics of a *Lactobacillus* suitable for use in a medicant of the present invention can be obtained by, for example, subjecting a parental strain to at least one round of chemical and/or radiation mutagenesis, to increase the rate of mutagenesis, thereby increasing the probability of obtaining a microorganism having improved desired characteristics. It will be obvious to one of skill in the art that mutant microorganisms of the present invention also include microorganisms that can be obtained by genetically engineering microorganisms to, for example, have increased percent VEC cohesion values. As used herein, a "mutated microorganism" is a mutated parental microorganism in which the nucleotide composition of such microorganism has been modified by mutation(s) that occur naturally, that are the result of exposure to a mutagen, or that are the result of genetic engineering.

Preferred species of *Lactobacillus* include *Lactobacillus crispatus*, *Lactobacillus gasseri* and *Lactobacillus jensenii*, or a species of *Lactobacillus* having 95% sequence homology to the 16S rRNA gene sequence of any of the identified species. Particularly preferred strains of lactobacilli are strains having all the identifying characteristics of the *Lactobacillus crispatus* CTV-05 strain, *Lactobacillus crispatus* SJ-3C strain. *Lactobacillus crispatus* CTV-05 is a preferred strain. Methods used to differentiate between *Lactobacillus* strains include Rep-PCR, as described in Antonio & Hillier, *J. Clin. Microbiol.* 2003, 41: 1881-1887, multilocus sequence typing (MLST), originally developed to identify strains of pathogens (see, e.g., Maiden, M. C., et. al. 1998, Multilocus sequence typing: a portable approach to the identification of clones within populations of pathogenic microorganisms. *Proc. Natl. Acad. Sci. USA.*, 95:3140-2145), and whole genome sequencing.

Preparation of *Lactobacillus* Species

The *Lactobacillus* strains useful for the present invention can be grown in any suitable liquid or on solid media (e.g., agar). Bacterial media for growing *Lactobacillus* strains useful for the present invention are known and commercially available (e.g., from BD Difco) and include, e.g., de Man, Rogosa, and Sharpe (MRS) and Rogosa media. The *Lactobacillus* are preferably cultured anaerobically or microaerophilically and the temperature of the culture medium can be any temperature suitable for growth of *Lactobacillus*. *Lactobacillus* strains for the instant invention can be cultured in anaerobic conditions and are generally grown at about 37° C. Effective culture conditions for vaginal *Lactobacillus* strains useful for the instant invention are well known in the art. Specific culture conditions, culture media and methods of culturing *Lactobacillus* strains, particularly *L. crispatus* and *L. gasseri*, can be found in, e.g., U.S. Pat. Nos. 8,329, 447, 6,093,394, and Davis, C. Enumeration of probiotic strains: Review of culture-dependent and alternative techniques to quantify viable bacteria. *J Microbiol Methods.* 2014; 103:9-17.

The culture medium is inoculated with an actively growing culture of the *Lactobacillus* strain in an amount sufficient to produce, after a reasonable growth period, a suitable cell density (or potency) for transfer to the preservation medium. A non-limiting example of a reasonable growth period of the *Lactobacillus* used herein is a generation time of between 1 to 2.5 hours. The cells are grown to a preferred cell density in the range of from about $10^8$ CFU/mL to about $10^{10}$ CFU/mL. A culture-based method is used to determine the cell density, in which serial dilutions of *Lactobacillus* cultures are plated onto MRS agar plates and incubated for 48 hr anaerobically at 37° C. Colonies on the plates are counted and the number of CFUs (colony forming units) in the samples are calculated as CFU/mL or CFU/gram. Methods of determining the CFUs are described in detail below.

Once the cells are grown to preferred cell density, the bacterial cells can be harvested using any suitable method to remove the cells from the culture media. Non-limiting exemplary methods for harvesting the cultured cells includes, filtration, centrifugation, and sedimentation. In some examples, harvesting cultured cells can involve hollow fiber filtration and washing via diafiltration. Methods for harvesting cultured *Lactobacillus* cells are well known in the art and are described in detail in the Examples section. After separation of the cells from the culture media and/or washing of the biomass; the cells are centrifuged to form a cell pellet in preparation for suspension in a preservation medium.

The harvested *Lactobacillus* bacterial cell pellet or filtrate or biomass is resuspended in a suitable aqueous preservation medium, where the weight ratio of cell material wet weight (grams) to preservation media (mL) can be between 1:1 and 1:8 grams of cell material to milliliter of preservation media. In some embodiments, the bacterial cell material is resuspended in a suitable aqueous preservation medium, where the weight ratio of cell material wet weight (grams) to preservation media (mL) can be 1:1, 1:2, 1:3, 1:4, 1:5, 1:6, 1:7, or 1:8 grams of cell material to milliliter of preservation media. In some embodiments, the bacterial cell material is resuspended in a suitable aqueous preservation medium, where the weight ratio of cell material wet weight (grams) to preservation media (mL) can be between 1:1 and 1:3 grams of cell material to milliliter of preservation media.

The aqueous preservation medium is comprised of ingredients that minimize the damaging effects encountered during the preservation process. A suitable preservation medium for use with the present invention can be any preservation medium known in the art. The particular preservation medium can be optimized for the particular *Lactobacillus* species and strain and the type of drying process used (if applicable). For example, if the bacterial preparation is to be freeze dried, then the preservation medium will include components known to protect against cryo-damage, such as trehalose or sucrose solutions. An exemplary preservation medium suitable for use with the present invention is disclosed in U.S. Pat. No. 6,372,209. Other preservation media suitable for use with the present invention are known to persons of skill in the art as disclosed in U.S. Pat. Nos. 5,614,209; 7,122,370; and 6,610,531. A preservation matrix suitable for use with the present invention is able to maintain genetically stable microorganisms for at least 2 years in vitro at 2-8° C. Additional drying methodologies and protective agents are disclosed in the review by Morgan et al. (2006) *J. Microbiol. Meth.* 66:183-193.

In some embodiments, the preservation medium that is particularly useful for the invention is free of animal-derived products and includes a carbohydrate, a polyol, an antioxidant, a buffering agent, and, optionally, an amino acid. Non-limiting exemplary carbohydrates suitable for use with the preservation medium include trehalose, dextrose, lactose, maltose, sucrose and/or any other disaccharide or polysaccharide. Non-limiting exemplary polyols suitable for use with the preservation medium include xylitol, adonitol, glycerol, dulcitol, inositol, mannitol, maltitol, isomalt, lactitol, erythritol, sorbitol and/or arabitol. Non-limiting exemplary antioxidants suitable for use with the preservation medium include sodium ascorbate, ascorbic acid, palmityl ascorbate, propyl gallate and vitamin E ($\alpha$-tocopherol). Non-limiting exemplary buffering agents suitable for use with the preservation medium include sodium phosphate, disodium phosphate, potassium phosphate, sodium bicarbonate, histidine, arginine and sodium citrate. In some embodiments, the optional amino acid can be in the salt form of a suitable amino acid. Non-limiting exemplary amino acids and/or their salts suitable for use with the preservation medium include sodium glutamate, glutamine, glycine, arginine, histidine, and lysine.

In some embodiments, the preservation medium useful for the present invention includes a carbohydrate that is between about 5% and 20% of the preservation medium by weight per volume, a polyol that is between about 2% and 9% of the preservation medium by weight per volume, an antioxidant that is between about 0.5% and 1.5% of the preservation medium by weight per volume, a buffering agent that is between 10 mM and 50 mM, and, optionally, an amino acid that is between about 0% and 5% of the preservation medium by weight per volume. In other embodiments, a preservation medium suitable for use with the present invention can include a carbohydrate that is between about 5% and 15% of the preservation medium by weight per volume, a polyol that is between about 2% and 7% of the preservation medium by weight per volume, an antioxidant that is between about 0.5% and 1.0% of the preservation medium by weight per volume, a buffering agent that is between 10 mM and 30 mM, and, optionally, an amino acid that is between about 0% and 5% of the preservation medium by weight per volume.

In some embodiments, a particularly useful preservation medium for use with the present invention includes trehalose as the carbohydrate that is between about 5% and 20% of the preservation medium by weight per volume, xylitol as the polyol that is between about 2% and 9% of the preservation medium by weight per volume, sodium ascorbate as the antioxidant that is between about 0.5% and 1.5% of the preservation medium by weight per volume, sodium phosphate as the buffering agent that is between 10 mM and 50 mM, and, optionally, sodium glutamate as the amino acid that is between about 0% and 5% of the preservation medium by weight per volume. In other embodiments, a particularly useful preservation medium suitable for the present invention includes trehalose that is between about 5% and 15% of the preservation medium by weight per volume, xylitol that is between about 2% and 7% of the preservation medium by weight per volume, sodium ascorbate that is between about 0.5% and 1.0% of the preservation medium by weight per volume and sodium phosphate that is between 10 mM and 30 mM. In some other embodiments, a preservation medium suitable for use with the present invention includes trehalose that is between about 5% and 15% of the preservation medium by weight per volume, xylitol that is between about 2% and 7% of the preservation medium by weight per volume, sodium ascorbate that is between about 0.5% and 1.0% of the preservation medium by weight per volume, sodium phosphate that is between 10 mM and 30 mM, and, optionally, sodium glutamate that is between about 0% and 5% of the preservation medium by weight per volume.

Upon introduction of the harvested *Lactobacillus* cells to the preservation medium described herein, the resulting mixture is referred to as the cell-preservation medium slurry or wet drug formulation. In some embodiments, a cell-preservation medium slurry (i.e., wet drug formulation) can have an activity of between $10^8$ CFU/mL and $10^{11}$ CFU/mL. A more preferred cell-preservation medium slurry can have an activity of at least about $10^{10}$ CFU/mL. It is to be understood that one of ordinary skill in the art will appreciate variations to the basic culturing, harvesting and suspending steps disclosed herein and as such, the present invention incorporates such variations.

The cell-preservation medium slurry described above can be refrigerated and used as a liquid (i.e., wet drug formulation) or dried and used as a bulk drug powder (i.e., dry drug formulation). The cell-preservation medium slurry can be dried using any suitable drying method known in the art. Drying methodologies and protective agents are disclosed in the review by Morgan et al. (2006) *J. Microbiol. Meth.* 66:183-193. Suitable drying methods include air drying, vacuum drying, oven drying, spray drying, flash drying, thud bed drying, controlled atmosphere and lyophilization (i.e., freeze drying). In some embodiments, a desiccant is used to aid in the drying process, and/or to prevent reabsorption of moisture into the dried formulation. In some embodiments, the drying is carried out using a lyophilizer (i.e., Virtis, SP Scientific). Detailed freeze-drying methods known to persons of skill in the art and are disclosed in U.S. Pat. Nos. 6,093,394; 8,329,447; and 8,642,029. The potency of the bulk dry powder can be between $10^9$ CFU/g and $10^{12}$ CFU/g. A more preferred bulk powder can have an activity of at least about $10^{10}$ CFU/g.

The *Lactobacillus* formulations (wet and/or dry) of the present invention are tested for potency at different times throughout the preparation process using any suitable method known in the art. Such methods used to determine the potency that of the *Lactobacillus* formulations include, but are not limited to, the culture-based method, the details of which are disclosed in Brugger, S. D., et al. Automated Counting of Bacterial Colony Forming Units on Agar Plates. *PLOS ONE* 2012; 7(3): e33695. The light scattering method for determining cell density of *Lactobacillus* is used to monitor the fermentation process and involves measuring the optical density at 600 nm of a sample of bacteria.

The wet or dry bulk *Lactobacillus* drug formulations from the above-described methods are typically tested for purity and identity. The purity of the *Lactobacillus* drug formulations is determined using methods well known in the art and as described in United States Pharmacopeial Method <61> Microbial Enumeration Tests and United States Pharmacopeial Method <62> Tests for Specified Microorganisms. Genetic identification of the *Lactobacillus* species in the drug formulations is carried out by isolating genomic DNA using a commercially available kit (e.g. Power Soil DNA Isolation Kit, Mo Bio), amplifying the 16S rRNA gene using specific primers by PCR, sequencing the gene using a commercial DNA sequencing service (MCLAB), and comparing the sequence to a reference standard. Identification of the *Lactobacillus* strain in the formulations is determined using methods well known in the art, such as Repetitive Sequence Polymerase Chain Reaction (Rep-PCR) and as described in U.S. Pat. Nos. 6,093,3941; 8,329,447; and 8,642,029.

In order to adhere to the potency and dosage guidelines agreed upon and developed by the U.S. Food and Drug Administration (FDA), the activity of the bulk *Lactobacillus* drug formulation is diluted using a pharmaceutically acceptable excipient. Any suitable inactive pharmaceutically acceptable excipient (i.e., diluent) known in the art can be used to dilute the potency of the *Lactobacillus* drug formulation. Diluted *Lactobacillus* drug formulations are referred to as the liquid drug product (from the bulk wet formulation) or the powder drug product (from the bulk dry formulation). In some embodiments, the diluent can be maltodextrin, pre-gelatinized starch, sucrose, lactose, Pharmasperse®, mannitol, xylitol, microcrystalline cellulose, crospovidone, dibasic calcium phosphate, or a combination thereof. In other embodiments, maltodextrin or pre-gelatinized starch can be used to dilute the bulk dry formulation. In some embodiments, maltodextrin is used to dilute the bulk dry formulation. A suitable diluent is used to reduce the potency of the *Lactobacillus* drug formulations to between $10^8$ CFU and $10^{11}$ CFU per dose, or between $10^8$ CFU and $10^{10}$ CFU per dose. A more preferred drug product (liquid or powder) can have an activity of greater than $10^9$ CFU per dose.

Administration of *Lactobacillus* Species

A woman diagnosed with AVM is administered *Lactobacillus* described above in combination with (e.g., simultaneously with, before, and/or after) the administration of an antibiotic described above and before and/or after embryo transfer in an amount sufficient to colonize the vaginal mucosa. The *Lactobacillus* species can be administered 1 or 2 times per day. In some embodiments, the administration of the *Lactobacillus* is during the final few days of the administration regimen of an antibiotic (i.e., 2 to 4 days before the completion of the administration regimen of an antibiotic). In some embodiments, the *Lactobacillus* is administered after an antibiotic has been administered for 2, 3, 4, 5, 6, or 7 days. In some embodiments, the *Lactobacillus* is administered after an antibiotic has been administered for about 7 days. In some embodiments, the *Lactobacillus* is administered after an antibiotic has been administered for at least 5 days.

In some embodiments of the invention, the *Lactobacillus* species can be administered for between 1 and 14 days after the completion of the administration regimen of an antibiotic and before embryo transfer or zygote transfer. In other embodiments, the *Lactobacillus* species can be administered for 1, 2, 3, 4, 5, 6, 7, 10, 12, or 14 days after the completion of the administration regimen of an antibiotic. In particular embodiments, the *Lactobacillus* species can be administered for between 5 and 7 days after the completion of the administration regimen of an antibiotic. In another embodiment, the *Lactobacillus* species can be administered for 7 days after the completion of the administration regimen of an antibiotic.

The *Lactobacillus* drug product is administered at between $10^8$ CFU and $10^{11}$ CFU per dose, or between $10^8$ CFU and $10^{10}$ CFU per dose. In other embodiments, the *Lactobacillus* is administered at a dose of at least $10^9$ CFU per day. The *Lactobacillus* drug product (i.e., *Lactobacillus*) is administered in dosages of between about 100 mg and 600 mg, or of about 150, 200, 250, 300, 350, 400, 450, 500, or 550 mg. In other embodiments, the *Lactobacillus* drug product can be administered in dosages of between about 150 mg and 450 mg, or about 150 mg and about 400 mg, or about 150 mg and about 350 mg. In some embodiments, the *Lactobacillus* drug product can be administered in dosages of between about 150 mg and 250 mg. In a particular embodiment, the *Lactobacillus* drug product can be administered in a dosage of about 200 mg. In some embodiments, the *Lactobacillus* drug product can be administered as a dry powder composition.

In Vitro Fertilization

A human zygote or embryo is transferred to a woman diagnosed with AVM and undergoing in vitro fertilization after the administration of an antibiotic and *Lactobacillus* as described above. In general, an embryologist transfers embryos to a woman through the cervical canal using a soft transfer catheter. The catheter is preferably placed 1-2 cm from the uterine fundus before expelling the contents and depositing the embryos. Methods and procedures involving zygote or embryo transfer are known to those of skill in the art. See, for example, U.S. Pat. No. 7,781,207 and U.S. patent application Ser. No. 13/655,257.

The embryo transfer or zygote transfer occurs after the *Lactobacillus* species has been administered as described above. For example, the embryo transfer or zygote transfer can occur after the *Lactobacillus* has been administered once daily for 7 days at between $10^8$ CFU and $10^{11}$ CFU per dose, where each dose is between about 150 mg and 250 mg. After completion of the embryo transfer or zygote transfer, the *Lactobacillus* can be optionally administered as a second treatment at between $10^8$ CFU and $10^{11}$ CFU per dose for an additional period of time. The second dose of *Lactobacillus* can be administered in any *Lactobacillus* dosage amount described above. The second *Lactobacillus* treatment can be administered in the same dose as the first *Lactobacillus* treatment or a different dose as the first *Lactobacillus* treatment. For example, following the completion of the embryo transfer or zygote transfer, the dose of *Lactobacillus* used prior to the embryo transfer or zygote transfer can be administered again between 1 and 5 times per week. In some embodiments, the second dose of *Lactobacillus* can be administered 1, 2, 3, 4, or 5 times per week after the completion of the embryo transfer or zygote transfer. In other embodiments, the dose of *Lactobacillus* can be administered between 1 and 4 times per week, or between 2 and 5 times per week, or between 1 and 3 times per week, or between 1 and 2 times per week after the completion of the embryo transfer or zygote transfer. In a particular embodiment, the dose of *Lactobacillus* can be administered twice per week after the completion of the embryo transfer or zygote transfer. The second *Lactobacillus* treatment can be administered as a dry composition or a wet composition.

The duration of the second *Lactobacillus* treatment (i.e., post-embryo transfer/post-zygote transfer) is between 1 and 14 weeks, and until a pregnancy scan indicates successful implantation of the embryo or zygote. For example, the second *Lactobacillus* treatment can be administered for between 2 and 13 weeks, or 3 and 12 weeks, or 4 and 11 weeks, or 5 and 10 weeks, or 6 and 9 weeks, or 7 and 8 weeks after the completion of the embryo transfer or zygote transfer. In particular embodiments, the second *Lactobacillus* treatment can be administered for between 5 and 10 weeks after the completion of the embryo transfer or zygote transfer. In another embodiment, the second *Lactobacillus* treatment can be administered for 7 weeks after the completion of the embryo transfer or zygote transfer. In another embodiment, the duration second *Lactobacillus* treatment is for 7 weeks and until a pregnancy scan indicates successful implantation of the embryo or zygote.

After completion of the embryo transfer or zygote transfer, a pregnancy scan is typically performed. In some cases, a pregnancy scan is performed after completion of the second *Lactobacillus* treatment (i.e., post-embryo transfer/post-zygote transfer) as described above. A pregnancy scan can be a biochemical pregnancy scan or a clinical pregnancy scan. Because hCG levels tend to rise within a few weeks of embryo or zygote implantation, a biochemical pregnancy scan showing hCG levels above at least 25 mtU/mL can indicate a biochemically detectable pregnancy. Detection of a certain level of hCG may be accomplished earlier in blood than in urine. In some embodiments, a biochemical pregnancy scan can be performed at least 7 to 30 or more days after embryo transfer or zygote transfer. In other embodiments, a biochemical pregnancy scan can be performed 14 to 21 days after embryo transfer or zygote transfer. In some embodiments, a biochemical pregnancy scan can be performed after completion of the second *Lactobacillus* treatment as described above.

In some embodiments, the pregnancy scan is a clinical pregnancy scan. A clinical pregnancy scan is an assessment of the woman into which an embryo or zygote has been transferred using an ultrasound scan or Doppler testing. The presence of a gestational sac and/or heart motion indicates successful implantation and a clinical pregnancy. In some embodiments, a clinical pregnancy scan is performed after completion of the embryo transfer or zygote transfer. In some embodiments, a clinical pregnancy scan can be performed 7 to 14 or more weeks after embryo transfer or zygote transfer. In other embodiments, a clinical pregnancy scan can be performed 6 to 8 weeks after embryo transfer or zygote transfer. In some embodiments, a clinical pregnancy scan can be performed 7 weeks after embryo transfer or zygote transfer. In some embodiments, a clinical pregnancy scan can be performed after completion of the second *Lactobacillus* treatment as described above.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

IV. EXAMPLES

The following examples are provided by way of illustration only and not by way of limitation. Those of skill will readily recognize a variety of noncritical parameters which could be changed or modified to yield essentially similar results.

Example 1. Preparing the Dry Composition of *Lactobacillus*

This example details the general strategy for preparing a dry composition of *Lactobacillus* in powder form as a medical product, involving bacterial cultivation, suspension in preservation medium, drying, dilution, and packaging. The procedure described here, for the culture and processing of *Lactobacillus crispatus* SJ-3C, is applicable for any microorganism suitable for use with the present invention.

The initial *Lactobacillus crispatus* SJ-3C (SJ-3C) cells can be obtained from the deposit American Type Culture Collection (ATCC) under ATCC number PTA-10138. A Master Cell Bank and Working Cell Bank of these cells are prepared and can be subsequently used in the preparation of the dry *Lactobacillus* compositions.

The SJ-3C cells are initially plated onto modified de Man, Rogosa, and Sharpe (MRS) agar plates and grown under anaerobic conditions for 72 hours at 37° C. Cells from the plates are inoculated into 10 mL of modified MRS and incubated anaerobically for 24 hours at 37° C. This culture is then transferred to 490 mL of growth medium and incubated for 24 hours at 37° C., followed by transfer to 4.5 L of medium in a 5 L Bellco Bioreactor. The 5-liter culture is incubated anaerobically at 37° C. for an additional 24 hours to serve as the fermentor inoculum.

Fermentation is performed in a fermentor (100 L fermentor) at pH 6.0 in the presence of modified MRS medium sparged with nitrogen gas. Fermentation is initiated by addition of the inoculum and completed after approximately 15 hours when the cells reach early stationary phase and growth stops. At this point, glucose is depleted, lactic acid production stops, the optical density of the culture at 600 nm (OD600) remains constant and the cells are harvested.

Cells are harvested, concentrated, and washed by buffer exchange into phosphate-buffered saline (diafiltration) in a sterile closed hollow fiber system using a tangential flow membrane. When the residual lactate concentration reaches 10% of the starting value at harvest and pH of the permeate remains constant, the cells are aseptically removed from the harvest system and collected by centrifugation at 1500×g for 20 minutes, 2-8° C.).

Cell pellets are resuspended in a preservation medium solution, using 2.5 mL of preservation solution per gram of cell paste. The preservation medium solution contains 15% trehalose, 6% xylitol, and 1% sodium ascorbate in a 10 mM sodium phosphate buffer (pH 7.4), which is used to prepare batches of the harvested SJ-3C slurry. The resulting batches of the preservation medium cell slurry are to have calculated activities of between $1 \times 10^{10}$ CFU/mL and $1 \times 10^{11}$ CFU/mL. The slurry is transferred to sterile Lyoguard™ trays and lyophilized in a Virtis Genesis Lyophilizer. Viability of the cell slurry is determined prior to lyophilization by plate counting. The Lyoguard™ trays containing the cell cakes are placed in heat-sealed bags with desiccant and purged with nitrogen gas, and held at 2-8° C. until milling.

The SJ-3C bulk drug substance is produced by milling the lyophilized cell cakes with 0.5% colloidal silicon dioxide as an anti-caking agent using a cone mill. The bulk powder is purged with nitrogen ($N_2$) gas and stored with desiccant in a heat-sealed bag at 2-8° C. until used for manufacture of the drug product. The SJ-3C bulk drug substance is tested for purity, potency (CFU), identity, and residual moisture using the methods as described previously and those known to one of skill in the art. The ideal activity of the resultant batches of the dry SJ-3C bulk drug substance should be between $5 \times 10^{19}$ CFU/g and $1.0 \times 10^{11}$ CFU/g. The ideal water activity of the dry SJ-3C bulk drug substance should be <0.220. When tested for purity, the resulting SJ-3C bulk drug substance will contain <200 CFU/g of total aerobic counts, <20 CFU/g of total yeasts and molds, and an absence of objectionable organisms. The identity of the resulting SJ-3C bulk drug substance is confirmed by the 16S rRNA gene sequence.

The bulk drug substance is diluted by 3 to 10-fold with maltodextrin to give a final dose of $2 \times 10^9$ CFU/dose to $5 \times 10^9$ CFU/dose. The dose is 200 mg. One dose of the diluted drug substance is placed in a medical powder applicator and packaged as the final drug product.

Example 2. Comparison of Preservation Media with and without Animal-Derived Excipients The following example demonstrates the development a preservation medium for a dry powder *Lactobacillus crispatus*. The example illustrates the increased stability of a dry *Lactobacillus* powder when animal-derived excipients are eliminated from the preservation medium.

For development of a formulation for lyophilization, batch fermentation of *Lactobacillus crispatus* SJ-3C is performed in a stirred bioreactor containing 1 L of modified MRS medium at pH 6.0. The cells are harvested in early stationary phase at the completion of fermentation. The batch process typically yields between $1.0 \times 10^9$ and $1.5 \times 10^9$ CFU/mL with >90% cell viability. The cells are recovered by centrifugation, washed with phosphate buffered saline, and mixed with one or more preservation solutions for lyophilization. A major goal is to identify a formulation without skim milk with good room temperature stability. The mixtures are then freeze-dried in a Virtis Advantage lyophilizer. The lyophilized cakes are manually powdered, placed in foil pouches with desiccant, purged with $N_2$, heat sealed and stored at 25° C. Representative results from this procedure are shown in FIG. 1, in which *Lactobacillus crispatus* strain CTV-05 was used.

Powder samples were removed at regular intervals and activity measured by plating on MRS agar and colony counting. The best combination of cryoprotection and room temperature stability was achieved using a preservation solution containing 15% trehalose, 6% xylitol, 1% sodium ascorbate, and 10 mM sodium phosphate at pH 7.4 (FIG. 1, upper line). This formulation provided better stability than the same formulation containing 5% skim milk (FIG. 1, lower line).

Example 3. Use of Sodium Glutamate to Improve Stability

Figure 2:
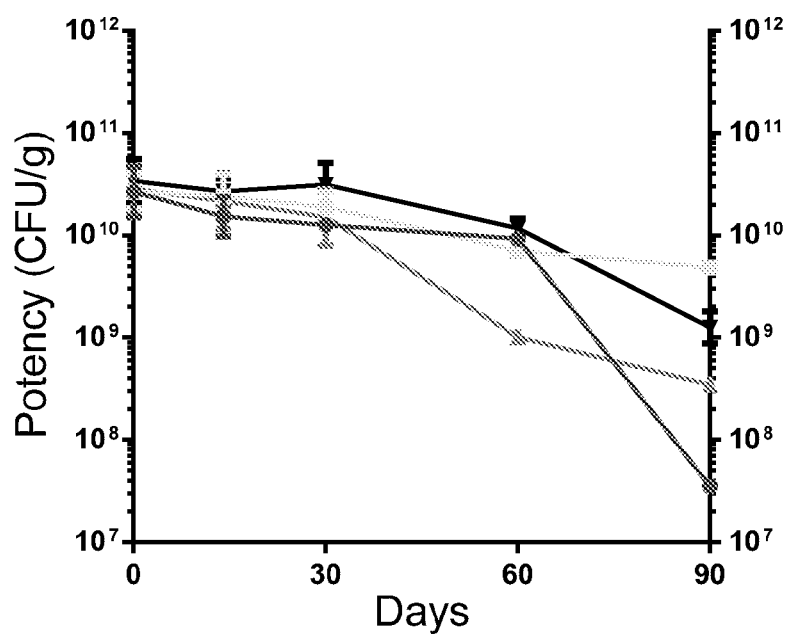
FIG. 2. *Lactobacillus* powder formulations with sodium glutamate or without sodium glutamate. The accelerated stability of four LACTIN-V formulations without sodium glutamate (circles, triangles) or with sodium glutamate (squares, inverted triangles) at 37° C. was determined by measuring viability over time. Powder samples were stored at 37° C. for 90 days and viability determined at different time points by culturing on MRS agar plates and counting colonies.

Following the procedure of Example 2, cultured *L. crispatus* CTV-05 (LACTIN-V) cells were formulated in four different preservation media: 1) 15% trehalose, 6% xylitol, 1% sodium ascorbate and 10 mM sodium phosphate at pH 7.4 (triangles); 2) the same preservation medium as 1), and additionally 5% sodium glutamate (inverted triangles); 3) 12% trehalose, 8% xylitol, 1% sodium ascorbate and 10 mM sodium phosphate at pH 7.4 (circles); and 4) the same preservation medium as 3), and additionally 5% sodium glutamate (squares). As shown in FIG. 2, the sodium glutamate improved the stability of both powder formulations at elevated temperatures (37° C.), while having no effect on the initial cryopreservation.

Example 4. Treatment of Diverse Vaginal Microbiota in Rhesus Macaques Models

The vaginal microbiome of the rhesus macaque is typically diverse with low levels of *Lactobacillus*, similar to the abnormal vaginal microbiota in humans. Because of this similarity, the effects of antibiotic pre-treatment on human vaginal *Lactobacillus* colonization was studied in the rhesus macaque model.

Figure 3:
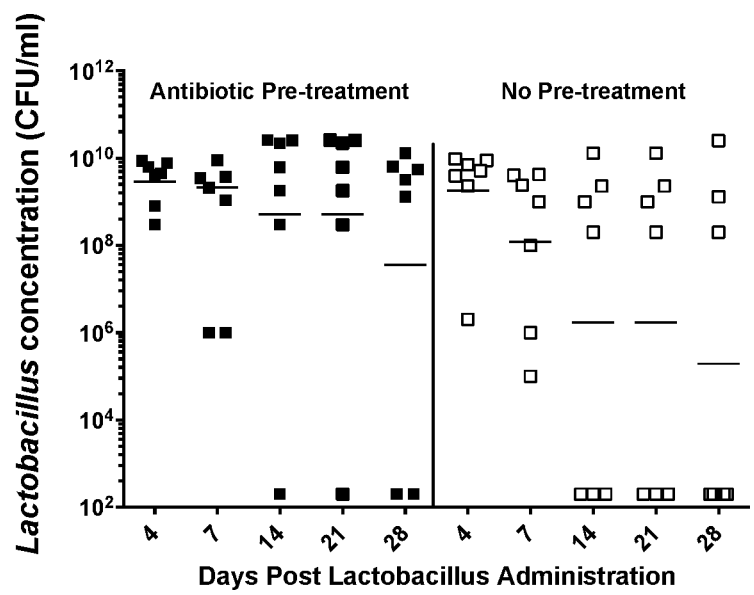
FIG. 3. The effect of antibiotic pre-treatment on vaginal *Lactobacillus* colonization levels (CFU/mL) in rhesus macaques after 4, 7, 14, 21, and 28 days post-*Lactobacillus* administration. Each square represents an individual macaque. Macaques pre-treated with antibiotic are represented by black squares; macaques not pre-treated with antibiotic are represented by white squares. The horizontal bars represent the median CFU/ml at each time point.

Seven female rhesus macaques were treated once a day for 5 days with 200 mg of intravaginal azithromycin, followed by intravaginal administration of $10^{10}$ CFU/dose of human *Lactobacillus jensenii* 1153 once daily for 5 days. For comparison, another group of seven macaques were treated for 5 days with intravaginal *L. jensenii*, but were not pre-treated with antibiotic. Vaginal fluid samples were collected on days 4, 7, 14, 21, and 28 post-*Lactobacillus* administration to evaluate colonization levels of *Lactobacillus*. *Lactobacillus* were enumerated by culturing samples on MRS agar plates and counting colonies, and the resulting *L. jensenii* concentrations were expressed as colony forming units (CFU)/ml. As shown in FIG. 3, antibiotic pre-treatment of a diverse vaginal microbiota (typical of macaques) can improve the vaginal colonization of a non-native human vaginal *Lactobacillus* over time.

Figure 4:
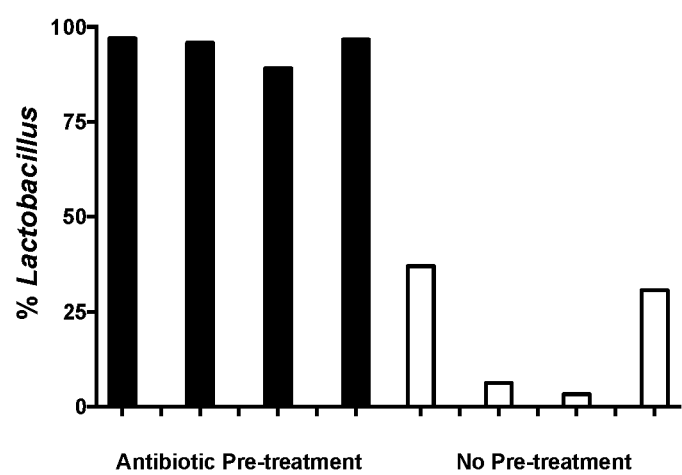
FIG. 4. The percentage of *Lactobacillus* in the vaginal microbiota in each rhesus macaque, analyzed by 16S-rRNA gene-based vaginal microbiome analysis after two weeks post-*Lactobacillus* administration. Each bar represents an individual macaque. Macaques pre-treated with antibiotic are represented by black bars; macaques not pre-treated with antibiotic are represented by white bars.

In a similar experiment, four female rhesus macaques were treated once a day for 5 days with 200 mg of intravaginal azithromycin, followed by intravaginal administration of $10^{10}$ CFU/dose of human *Lactobacillus jensenii* 1153 once daily for 5 days. For comparison, another group of four macaques were treated for 5 days with intravaginal *L. jensenii*, but were not pre-treated with antibiotic. The composition of the vaginal microbiome for each macaque was analyzed by 16S rRNA gene sequencing of vaginal bacteria collected approximately 2 weeks post-*Lactobacillus* administration. The results of this 16S rRNA analysis are shown in FIG. 4, and represent the percentage of *Lactobacillus* in the vaginal microbiota for each macaque. As shown in FIG. 4, antibiotic pre-treatment of a diverse vaginal microbiota (typical of macaques) can markedly increase the proportion of *Lactobacillus* in the microbiome, thus limiting competition by other strains.

This is the effect to be achieved in human women pre-treated with oral clindamycin and vaginal *L. crispatus*. The important observation is that pre-treatment with an antibiotic can markedly improve the ability of a non-native *Lactobacillus* to engraft itself into the vaginal microbiome of a subject with abnormal (diverse) vaginal microbiota (like a rhesus macaque). As a result, sustained vaginal colonization of *Lactobacillus* is improved, abnormal microbiota reduced, and IVF success rate (associated with *Lactobacillus*-dominated microbiota) will be improved.

Example 5. Treatment of Abnormal Vaginal Microbiota for Increasing IVF Success Rates A female patient between the age of 18 and 42 years old suffering from infertility attends a fertility clinic. Notwithstanding infertility, the female patient is asymptomatic. The asymptomatic female patient is tested for the presence of abnormal vaginal microbiota using the qPCR diagnostic method targeting *Gardnerella vaginalis* and/or *Atopobium vaginae*. The qPCR diagnostic tests detect the presence of

*Gardnerella vaginalis* above the threshold of 5.7×10⁷ copies/mL and the presence of *Atopobium vaginae* above the threshold of 5.7×10⁶ copies/mL, resulting in a positive AVM diagnosis in the patient.

The female patient having been diagnosed with AVM using the qPCR test receives an antibiotic treatment with a 300 mg clindamycin oral capsule two times per day for 7 days. After completion of the clindamycin treatment, the female patient begins treatment using the *Lactobacillus crispatus* drug product in the form of a dry powder (i.e., LACTIN-V). The LACTIN-V powder is administered vaginally with a pre-filled applicator. Each pre-filled applicator contains a 200 mg dose of LACTIN-V at 2×10⁹ CFU/applicator. The female patient receives one dose of LACTIN-V daily for 7 consecutive days.

After completing the initial LACTIN-V treatment described above, the woman then undergoes embryo transfer. Following the completion of the embryo transfer, the woman is then administered a second LACTIN-V treatment, involving the administration of a 200 mg dose of LACTIN-V at 2×10⁹ CFU/applicator twice per week for 7 weeks until the female patient receives a clinical pregnancy scan, demonstrating the presence of a fetal heartbeat.

What is claimed is:

1. A method for improving the success rate of in vitro fertilization in women hosting abnormal vaginal microbiota comprising the steps of:
    i) selecting a woman suspected of hosting abnormal vaginal microbiota (AVM);
    ii) administering to the woman an antibiotic active against bacterial vaginosis associated bacteria, including *Gardnerella vaginalis* and *Atopobium vaginae*, for at least 5 days prior to step iii, wherein said antibiotic is administered in an amount and duration effective to reduce the quantity of abnormal vaginal microbiota hosted by the woman;
    iii) administering to the woman via vaginal administration an amount of *Lactobacillus* species, wherein the amount of *Lactobacillus* is sufficient to colonize the vaginal mucosa following the antibiotic administration of step ii, wherein the *Lactobacillus* species is selected from a group of species consisting of: *Lactobacillus crispatus*, *Lactobacillus jensenii* and *Lactobacillus gasseri*, wherein said species have the ability to produce greater than 0.5 ppm of hydrogen peroxide under effective culture conditions; and,
    iv) transferring a human zygote or embryo to the woman.

2. The method of claim 1, wherein the amount of *Lactobacillus* administered to the woman is daily and at between $10^8$ to $10^{10}$ CFU per dose.

3. The method of claim 1, wherein the antibiotic is selected from the group consisting of clindamycin and metronidazole.

4. The method of claim 1, wherein the woman has *Gardnerella vaginalis* and/or *Atopobium vaginae* levels above accepted thresholds defining AVM.

5. The method of claim 1, wherein the amount of *Lactobacillus* species administered to the woman is once daily for 7 days and at between $10^8$ to $10^{10}$ CFU per dose prior to embryo transfer (ET), followed by twice weekly at the same dose for 7 weeks until clinical pregnancy is determined by ultrasound and/or detection of a fetal heartbeat.

6. The method of claim 1, wherein the *Lactobacillus* species is administered as a dry composition.

7. The method of claim 6, wherein the *Lactobacillus* species is preserved in a medium without animal-derived components.

8. The method of claim 6, wherein the *Lactobacillus* species is suspended, prior to drying, in a aqueous preservation medium consisting essentially of:
    (a) trehalose at between 5-15%, w/v;
    (b) xylitol at between 2-7%, w/v;
    (c) sodium ascorbate 0.5-1.0%, w/v; and
    (d) sodium phosphate at between 10-30 mM.

9. The method of claim 1, wherein the *Lactobacillus* species is co-administered with the antibiotic.

10. The method of claim 1, wherein the administration of *Lactobacillus* species occurs after the completion of step ii.

11. The method of claim 1, wherein the *Lactobacillus* species is administered at least 7 days prior embryo transfer.

12. The method of claim 1, wherein the *Lactobacillus* species is *Lactobacillus crispatus*.

13. The method of claim 1, wherein the *Lactobacillus* species includes *L. crispatus* and at least one more species of *Lactobacillus*.

* * * * *